United States Patent
Kreiner et al.

(10) Patent No.: US 9,928,348 B2
(45) Date of Patent: Mar. 27, 2018

(54) MEDICINE DISPENSING SYSTEM

(71) Applicant: AT&T Intellectual Property I, L.P., Atlanta, GA (US)

(72) Inventors: Barrett M. Kreiner, Woodstock, GA (US); Jonathan L. Reeves, Roswell, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 0 days.

(21) Appl. No.: 14/977,210

(22) Filed: Dec. 21, 2015

(65) Prior Publication Data

US 2017/0177830 A1   Jun. 22, 2017

(51) Int. Cl.
*G06F 19/00* (2011.01)
*B65G 1/137* (2006.01)
(Continued)

(52) U.S. Cl.
CPC ........ *G06F 19/3462* (2013.01); *A61J 1/1437* (2013.01); *A61J 1/1468* (2015.05);
(Continued)

(58) Field of Classification Search
None
See application file for complete search history.

(56) References Cited

U.S. PATENT DOCUMENTS 6,010,492 A   1/2000   Jacobsen et al.
6,045,254 A   4/2000   Inbar et al.
(Continued)

FOREIGN PATENT DOCUMENTS

GB   2507812       5/2014
JP   2009544338   12/2009
(Continued)

OTHER PUBLICATIONS

"e-pill CompuMed MD3 Tamper Proof Pill Dispenser: Dispense up to 4x per day," e-pill, epill.com, Mar. 4, 2010 https://web.archive.org/web/20100324021339/http://www.epill.com/compumed.html Discloses pill dispenser that automatically dispenses the proper medication at the right time while other medications are locked in a tamper-proof container. Two secure and refillable plastic trays.
(Continued)

*Primary Examiner* — Timothy R Waggoner

(57) ABSTRACT

Devices, methods, and computer-readable media are disclosed for storing and neutralizing a medicine. For example, a device may include a chamber for storing a medicine, a neutralizing component coupled to the chamber, a transceiver for receiving an instruction to neutralize the medicine, and a control unit that includes a processor and that is coupled to the transceiver, where the control unit is for neutralizing the medicine by activating the neutralizing component when the instruction is received via the transceiver. In another example, a device may include a medicine chamber for storing a medicine, an intermediate chamber for storing a neutralizing agent to neutralize the medicine, where a first wall between the medicine chamber and the intermediate chamber comprises a fluid-soluble material, and an outer chamber for storing a fluid, where the intermediate chamber and the outer chamber share a second wall.

16 Claims, 4 Drawing Sheets

(51) Int. Cl.
   *A61K 31/215*   (2006.01)
   *A61J 1/14*     (2006.01)
   *A61J 1/20*     (2006.01)

(52) U.S. Cl.
   CPC .......... *A61J 1/2003* (2015.05); *A61K 31/215* (2013.01); *B65G 1/137* (2013.01)

(56) References Cited

U.S. PATENT DOCUMENTS

| | | | | |
|---|---|---|---|---|
| 6,087,548 | A * | 7/2000 | Levy | A61M 5/3205 588/249 |
| 6,259,654 | B1 | 7/2001 | De la Huerga | |
| 6,471,087 | B1 | 10/2002 | Shusterman | |
| 6,575,208 | B2 | 6/2003 | Sharon et al. | |
| 6,973,435 | B1 | 12/2005 | Sioufi et al. | |
| 8,490,795 | B2 * | 7/2013 | Ziemba | B65B 53/02 405/129.3 |
| 8,530,378 | B2 * | 9/2013 | Croskey | B41M 7/0009 503/201 |
| 9,089,661 | B2 | 7/2015 | Stuart et al. | |
| 2001/0050237 | A1 * | 12/2001 | Hacikyan | B65D 81/264 206/204 |
| 2003/0086338 | A1 | 5/2003 | Sastry et al. | |
| 2007/0023444 | A1 * | 2/2007 | Holloway | A61J 7/0481 221/7 |
| 2007/0095850 | A1 | 5/2007 | Meyer | |
| 2007/0186923 | A1 * | 8/2007 | Poutiatine | A61J 7/0481 128/200.14 |
| 2008/0027579 | A1 | 1/2008 | Van der Hoop | |
| 2009/0192648 | A1 | 7/2009 | Namineni et al. | |
| 2010/0013597 | A1 | 1/2010 | Determan et al. | |
| 2011/0226817 | A1 * | 9/2011 | Ortenzi | A61J 7/0472 222/424.5 |
| 2013/0088328 | A1 | 4/2013 | DiMartino et al. | |
| 2014/0074283 | A1 | 3/2014 | Blackburn | |
| 2014/0187842 | A1 | 7/2014 | Holaday et al. | |
| 2014/0278510 | A1 | 9/2014 | McLean et al. | |

FOREIGN PATENT DOCUMENTS

| | | |
|---|---|---|
| JP | 2010522126 | 7/2010 |
| WO | WO 99/32065 | 7/1999 |
| WO | WO 2012/143435 | 10/2012 |
| WO | WO 2012/143442 | 10/2012 |
| WO | WO 2013/033033 | 3/2013 |
| WO | WO 2015/181198 | 12/2015 |

OTHER PUBLICATIONS

"Tamperproof. Up to 6 Alarms per Day. Secure with Four Locks," e-pill, epill.com, Sep. 20, 2014 https://web.archive.org/web/20140920011844/http://www.epill.com/epillsafe.html Discloses an automatic tamper proof automatic pill dispenser with four locks (patent pending).

"UCapIt Controlled Access Pharmaceutical Vending Machines and Inventory Control Tracking Systems," UCapIt, ucapit.com, Jan. 24, 2015 https://web.archive.org/web/20150124045547/http://www.ucapit.com/inquiry/?Discloses "Controlled Access Pharmaceutical Dispensing" system to resolve current and potential control issues associated with inventory and distributing pharmaceuticals.

"How the Philips Medication Dispensing Service Works," Philips, managemypills.com, Jul. 19, 2009 https://web.archive.org/web/20090719055306/http://www.managemypills.com/content/ How_PMD_Works Discloses a programmable medication dispenser; medications are placed into individual cups, then loaded into the machine. The dispenser will dispense the medication that you have loaded for the senior, at the programmed times.

"Measurable improvements in medication management: Pyxis MedStation® system," Care Fusion, carefusion.com, 2011. http://www.carefusion.com/Documents/brochures/medication-supply-management/DI_Pyxis-MedStation-4000-System_BR_EN.pdf Discloses: "The Pyxis MedStation® 4000 system can help manage medications by automating the process throughout the hospital. This market proven system streamlines medication distribution,".

* cited by examiner

MEDICINE DISPENSING SYSTEM

The present disclosure relates generally to medicine dispensing systems, and more particularly, to devices, methods, and computer-readable media for storing and neutralizing medicines.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
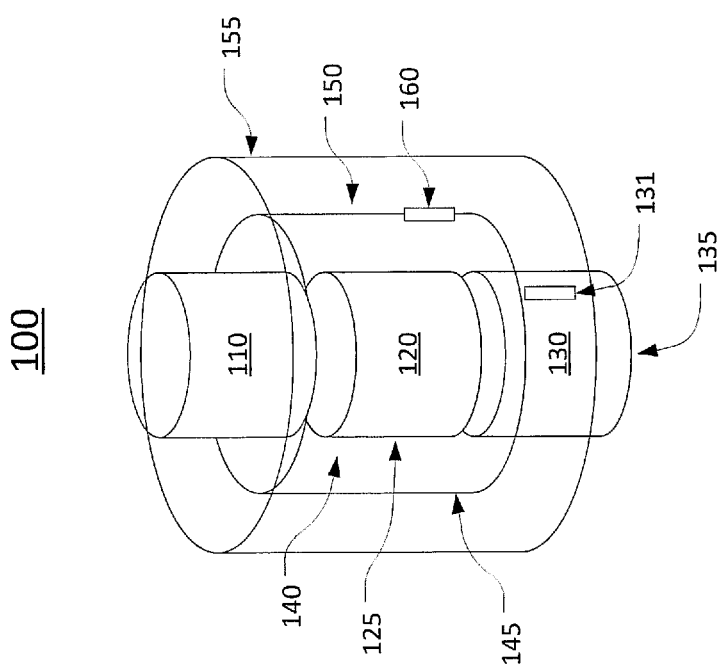
FIG. 1 illustrates an example device related to the present disclosure.
Figure 5:
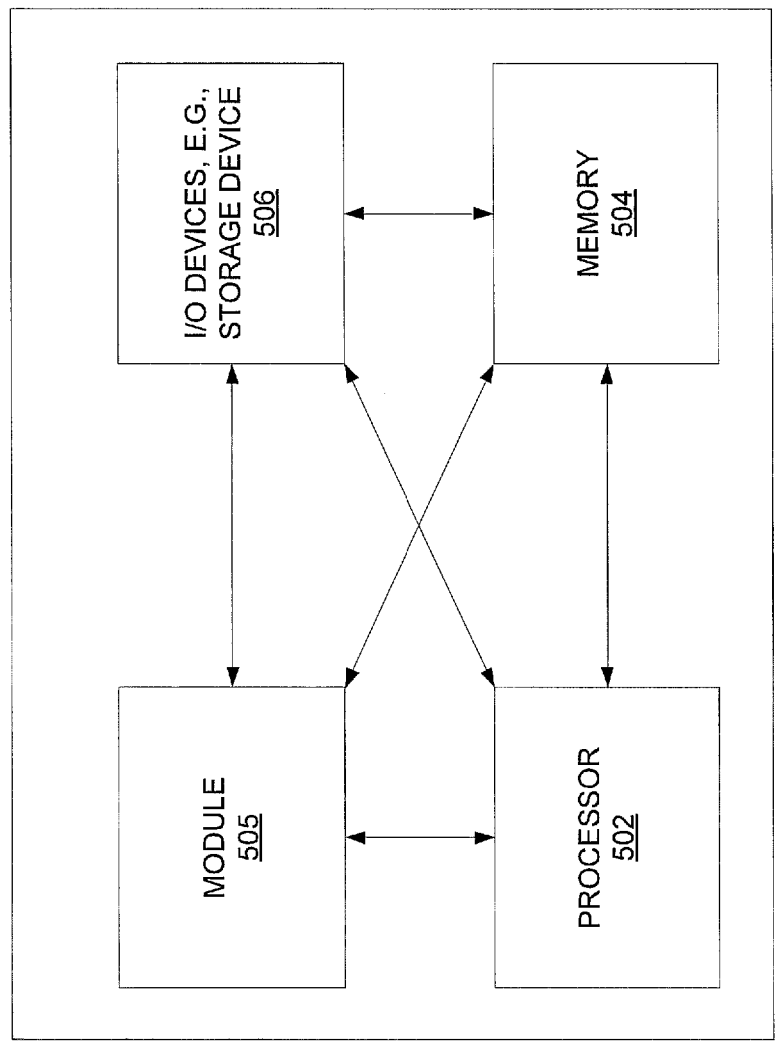
FIG. 5 illustrates an example high-level block diagram of a computer specifically programmed to perform the steps, functions, blocks, and/or operations described herein.

To aid in understanding the present disclosure, FIG. 1 illustrates an example container 100, e.g., a tamper-resistant container or storage device for storing a medicine. As illustrated in FIG. 1, the container 100 may include a first chamber for storing a medicine, e.g., a medicine chamber 120, and a second chamber for storing a neutralizing agent, e.g., an intermediate chamber 140. Container 100 may also include an outer chamber 150 for storing a fluid. In one example, container 100 may further include a control unit 130, e.g., an electronic control unit, and a testing module 110. In one example, the control unit 130 may include a dispensing channel 135 that is coupled to the medicine chamber 120 and which extends to an exterior portion of the device 100. In one example, the control unit 130 may comprise a computing device having a processor and a non-transitory computer readable medium, e.g., a memory, as illustrated in FIG. 5 and described in greater detail below. To prevent unauthorized access to the medicine in the medicine chamber 120, the dispensing channel 135 may be kept closed at all times other than when the medicine is to be dispensed according to a medicine dispensing schedule stored by the control unit 130. In one example, the outer chamber 150 and the intermediate chamber 140 share a wall 145. In addition, the intermediate chamber 140 and the medicine chamber 120 may share a wall 125. In one example, the wall 125 may comprise a fluid-soluble material, such as a gelatin, a paper, and so forth.

The fluid in the outer chamber 150, the neutralizing agent in the intermediate chamber 140, and the wall 125 comprising a fluid-soluble material may collectively comprise a tamper-resistance system, or tamper-proofing system for the device 100. To illustrate, a person may attempt to access the medicine in the medicine chamber 120 by drilling, piercing, puncturing, or cutting away at the device 100, beginning with the outer wall 155. The outer wall 155 may first be breached. In addition, to gain access to the medicine chamber 120 it may further be required to penetrate the wall 145. However, upon breaching the wall 145, e.g., via drilling, piercing, puncturing, or cutting, the fluid in the outer chamber 150 may be permitted to flow into the intermediate chamber 140. Once in the intermediate chamber 140, the fluid may come into contact with the neutralizing agent. The neutralizing agent may dissolve in the fluid or become suspended in the fluid. For instance, the neutralizing agent may be a dry neutralizing agent comprising a powder, one or more pellets or capsules, and so forth. Example neutralizing agents are described in greater detail below in connection with the example device 200 of FIG. 2. In addition to contacting the neutralizing agent, the fluid may also come into contact with the wall 125 comprising a fluid-soluble material between the intermediate chamber 140 and the medicine chamber 120. Notably, since the wall 125 is a fluid-soluble material, at least a portion of the wall 125 may dissolve upon contact with the fluid. Furthermore, the neutralizing agent may also be mixed with the medicine insofar as the wall 125 between the medicine chamber 120 and the intermediate chamber 140 storing the neutralizing agent may be dissolved and/or destroyed. In one example, the neutralizing agent may be stored in capsule form, where a shell of the capsule may be made from a same or similar material to that which is used for the wall 125. In one example, the fluid may also promote mixing and interaction of the neutralizing agent with the medicine to accelerate the neutralization of the medicine.

As mentioned above, in one example, device 100 may also include a testing module 110 for measuring and/or detecting various patient biometrics. Testing module 110 may take a variety of forms depending upon the particular type of medicine(s) stored in the medicine chamber 120 and/or upon the particular medical application associated with the device 100. For example, the testing module 110 may comprise a self-administered blood test unit, or may otherwise be configured to measure and/or detect various biomarkers in blood or other body fluids in an automated fashion. For instance, testing module may comprise an optical non-invasive monitor for blood glucose levels, oxygen levels, hemoglobin levels, etc. Testing module 110 may also comprise a detector for counting viral load in a body fluid, e.g., using real-time polymerase chain reaction (PCR). In still other examples, testing module 110 may comprise a device to measure pupil dilation, eye focus, etc. The foregoing are only several examples of a testing module 110. Thus, in other, further, and a different examples, testing module 110 may take a different form, or may include additional features to those described herein.

In one example, testing module 110 may be coupled to control unit 130, and may provide results of testing operations electronically to the control unit 130. For example, control unit 130 may store a medicine dispensing plan, e.g., a drug regimen to be administered to a subject (human or animal). The medicine dispensing plan may be to cause the control unit 130 to release a certain quantity of medicine in various doses at various times via the dispensing channel 135. However, the medicine dispensing plan may also include instructions to change a dosage, to change a time for an administering of a dose, and so forth depending upon various measurements that may be provided by the testing module 110. For instance, if after several days of administering a medicine, it is detected by the testing module 110 that a viral load has fallen to below a detectable threshold, the medicine dispensing plan may call for the dosage to be reduced or for the administration of the medication to end earlier than originally anticipated according to the medicine dispensing plan.

In one example, the control unit 130 may also include and/or may be coupled to a transceiver 131 for communicating with one or more external devices. For instance, the device 100 may be for use in connection with a dispensing machine. In addition, in one example the control unit 130 may be programmed at a hospital, a physician's office, a pharmacy, or in similar medical professional location to load a medicine dispensing schedule. The medicine may also be initially loaded into the medicine chamber 120 at a same location or at a different location. For instance, the medicine dispensing schedule may be loaded at a physician's office, while the medicine may be loaded in the medicine chamber 120 at a pharmacy. The control unit 130 may also be personalized to an intended recipient (e.g., a human patient). For example, the control unit 130 may include a lock mechanism such as a fingerprint activated lock, a keycode activated lock (where the keycode may be provided by a responsible medical professional to the patient), and so forth.

In one example, the transceiver 131 may comprise a transceiver for a Peripheral Component Interface express (PCIe) interface, for a serial connection, such as for a small component serial interface (SCSI), and so forth. For instance, the device 100 may plug-in to a dispensing machine or may be cable-connected to the dispensing machine. In another example, the transceiver 131 may comprise a wireless transceiver, e.g., for Institute of Electrical and Electronics Engineers (IEEE) 802.11, Bluetooth, and/or Bluetooth Low Energy (BLE) communications, and the like. Alternatively or in addition, the transceiver 131 may be for cellular communications. For instance, device 100 may receive instructions from a remove monitoring device via a cellular network and/or may report usage information to the remote monitoring device via the cellular network. These functions are described in greater detail below in connection with the example system 300 of FIG. 3.

Additional variations and enhancements to the device 100 may be provided in various examples of the present disclosure. In one example, medicine chamber 120 may store a variety of medicines which may be dispensed together, or in a staggered fashion, according to a medicine dispensing schedule. For instance, medicine chamber 120 may comprise multiple fluid-soluble walls to segregate different medicines. Upon an attempted unauthorized accessing of the medicines, the fluid from outer chamber 150 may contact with the multiple fluid-soluble walls, allowing a neutralizing agent, or multiple neutralizing agents stored in intermediate chamber 140 to come into contact with and be applied to the several medicines in order to neutralize and/or render the several medicines inert.

In one example, an opening unit 160 may also be included in the device 100. For example, opening unit 160 may comprise a door, a gate, a breakable seal, or the like which the control unit 130 can cause to open in order to allow the fluid in the outer chamber 150 to flow into the intermediate chamber 140 and to contact the wall 125 comprising the fluid-soluble material. For instance, the control unit 130 may receive a remote instruction from a monitoring device directing the control unit 130 to activate the tamper-protection system, e.g., to activate neutralizing agent. In still another example, the control unit 130 may implement a medicine neutralizing failsafe to neutralize the medicine after a certain period of time following an end of treatment. For instance, if it is determined that the medicine administering plan has come to an end and there is leftover medicine in the medicine chamber 120, the control unit 130 may be programmed to create an opening in the wall 145 via the opening unit 160 after 24 hours following the end of treatment, after 48 hours following the end of treatment, and so forth. In another example, the control unit 130 may be programmed to create an opening in the wall 145 via the opening unit 160 at a certain time or date after the device 100 is initially filled with the medicine, e.g., two-weeks after filling a prescription, 30 days after filling a prescription, etc. In still another example, the control unit 130 may create an opening in the wall 145 via the opening unit 160 when a tampering of the device 100 is detected via a separate electronic tampering detection unit (not shown). For instance, an electronic wire mesh may surround device 100 which, if breached, will electronically notify the control unit 130. In turn, control unit 130 may then cause opening unit 160 to generate a breach in the wall 145.

In still another example, testing module 110 may be omitted. For instance, in one example device 100 may be used in conjunction with a dispensing machine that may control metering of various doses of the medicine via the device 100. In addition, the dispensing machine may be equipped with one more testing devices for measuring/detecting various patient biometrics. For instance, a detection of a viral load of blood-borne pathogen via real-time PCR may require a machine that may be too bulky for convenient transportation. Thus, the testing equipment may be part of a dispensing machine, which may be relatively stationary, while the device 100 containing the medicine remains readily portable and can be filled and refilled at a pharmacy, a hospital, a clinic, or a physician's office, for example.

In addition, although examples of the present disclosure are described primarily in connection with a medicine storage and dispensing device that includes an on-board electronic control unit, other examples of the present disclosure may comprise a non-electronic device for storing, dispensing, and neutralizing a medicine. Alternatively, or in addition, a device of the present disclosure may include electronic components of a different nature than those described above in connection with the example of FIG. 1 and/or that perform different functions. To illustrate, a patient may be prescribed a medicine that is stored in a non-electronic device having a tamper-resistance system as described above, e.g., an outer chamber with a fluid, an intermediate chamber with a neutralizing agent, and a medicine chamber storing a medicine. The patient may access the medicine by using a key, a padlock, etc. While in this example, the patients may not be prevented from engaging in non-prescribed use of the medicine, the tamper-resistance system may nevertheless deter unauthorized access by persons other than the patient possessing the key or the lock code.

Figure 2:
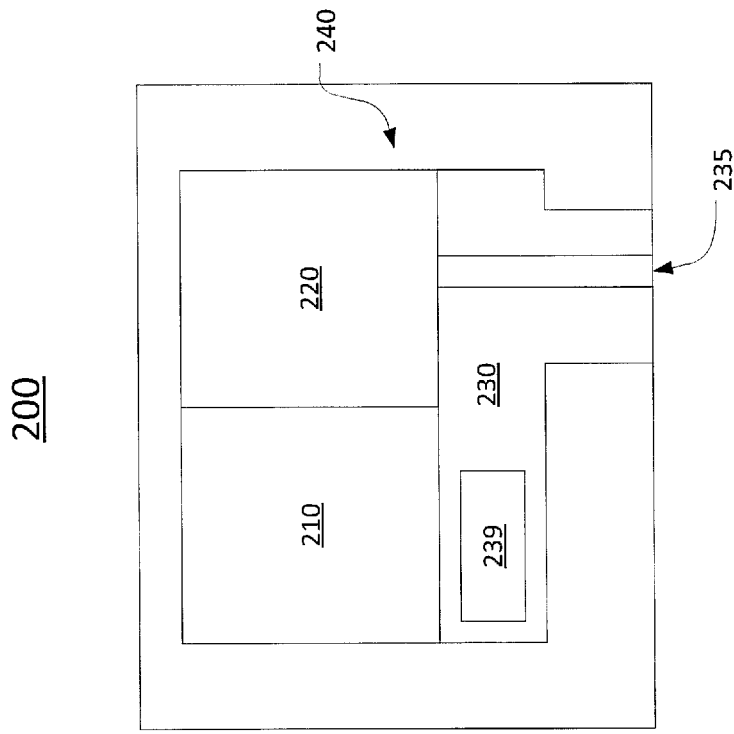
FIG. 2 illustrates an additional example device related to the present disclosure.

FIG. 2 illustrates an additional example device 200 of the present disclosure. As illustrated in FIG. 2, device 200 includes a chamber 220 for storing a medicine, a neutralizing component 210, and a control unit 230 to neutralize the medicine via the neutralizing component 210. Control unit 230 may include a dispensing channel 235 which may be opened by the control unit 230 when dispensing a medicine, but which is otherwise kept in a closed and locked state. In one example, the device 200 of FIG. 2 may represent the same or similar components to those described in connection with FIG. 1. For instance, the neutralizing component 210 may comprise a second chamber storing a neutralizing agent. In such an example, a fluid-soluble wall may be provided between chamber 220 and the neutralizing component 210, e.g., a second chamber. However, in another example, an electronic or electromechanical opening unit that is controllable by the control unit 230 may also be provided between chamber 220 and the neutralizing component 210 to create an opening in a shared wall.

In examples associated with the device 200 of FIG. 2, a neutralizing agent may comprise a dry neutralizing agent or may comprise a neutralizing agent in a gel, liquid, or fluid form. To illustrate, if the medicine is penicillin, amoxicillin, or a similar antibiotic, a neutralizing agent may comprise an amine-containing compound. In another example, if the medicine is aspirin, a neutralizing agent may comprise water. For instance, exposure to water may cause the aspirin to break down into acetic acid and salicylic acid. In still other examples, a neutralizing agent may comprise an oxidizing agent, such as hydrogen peroxide, hydrogen peroxide with iron, titanium dioxide, and so forth. The neutralizing agent may also comprise a disinfectant such, as chlorine dioxide, sodium hypochlorite, calcium hypochlorite, acetic acid, and the like.

A neutralizing component 210 of the device 200 may also take other forms. For instance, neutralizing component 210 may alternatively or additionally comprise an ozone generator, a heat source or a radiation source, e.g., including sources of optical frequencies and/or visible light, ultraviolet (UV) light including UVA, UVB, UVC, etc., infrared light, microwave radiation, and so forth. For instance, a heat source may comprise a lamp or other electro-resistive heater. A radiation source may also comprise a UV lamp for example, or an array of one or more UV light emitting diodes (LEDs). In general the nature of the neutralizing component may vary, e.g., depending upon the nature of the medicine and its susceptibility to certain conditions, and other factors, such as relative costs of different types of neutralizing components that may be effective in neutralizing, or rendering the medicine environmentally and/or biologically inert.

In one example, device 200 may include a tamper detection unit 240. For instance, the tamper detection unit 240 may comprise an electronic mesh surrounding other components of the device 200. For example, an electronic mesh may generate an electronic alarm signal if any filament of the electronic mesh is broken. In one example, the tamper detection unit 240 is coupled to the control unit 230 such that the control unit 230 may detect an attempted breach or other tampering with the device 200 via the alarm signal from the tamper detection unit 240. In other examples, tamper detection unit 240 may take a different form. For instance, tamper detection unit 240 may comprise a pressure sensor that may detect when a person may be attempting to pry off a lid of the device 200, open a locked door of the device 200, and so forth. In another example, the tamper detection unit 240 may comprise a keypad that opens with a correct passcode. Thus, for example, if one or more incorrect passcodes are entered on the keypad, the tamper detection unit 240 may generate an alarm signal for the control unit 230. In still another example, tamper detection unit 240 may comprise an optical sensor. For instance, if a person is attempting to pry off a lid or door of the device 200, this may allow some light to enter an interior area of the device 200 where an optical sensor of the tamper detection unit 240 may be situated. Accordingly, an alarm signal may be provided to the control unit 230 if a certain level of light is detected by such an optical sensor. Thus, in accordance with the present disclosure tamper detection unit 240 may take a number of different forms. For example, when a tampering of the device 200 is detected via the tampering detection unit 240, the control unit 230 may neutralize the medicine via the neutralizing component 210, e.g., by creating an opening in a wall separating the medicine from a neutralizing agent, by activating a heat or radiation source, and so forth.

In one example, device 200 may further include a transceiver 239 which may comprise a separate component, or which may be a part of the control unit 230 (broadly, the transceiver is coupled 239 is coupled to the control unit 230). The transceiver 239 may be a PCIe PHY, a SCSI transceiver, or the like. For instance, the device 200 may plug-in to a dispensing machine or may be cable-connected to the dispensing machine. In another example, the transceiver may comprise a radio frequency (RF) wireless transceiver, e.g., for IEEE 802.11, Bluetooth, and/or BLE communications, and the like. Alternatively or in addition, the transceiver may be a cellular transceiver. In one example, the transceiver 239 may be used by the control unit 230 to transmit a notification of a condition associated with the medicine to a medicine dispensing machine and/or a remote monitoring device. The notification may comprise, for example, a detection of a tampering of the device 200, or a detection of a treatment milestone in an administration of the medicine to a patient associated with the device 200. For example, device 200 may include a testing module (not shown), e.g., for measuring or detecting various patient biometrics. As such, the control unit 230 may determine, via such a testing module, that a patient's blood pressure has returned to an acceptable level, a viral load has fallen below detectable levels, and so forth. The control unit 230 may then send a notification to a remote monitoring device through a cellular or other wireless interface, via a connection to a medicine dispensing machine, and so on. However, in another example, the control unit 230 may send notifications of various measurements and test results without concluding that a particular medical milestone is detected. For instance, it may be left to a medical professional to interpret the measurements and test results to determine whether a medical milestone is achieved.

In addition, the control unit 230 may receive an instruction back from the remote monitoring device and/or from the medicine dispensing machine via the transceiver 239 in response to a notification that may be sent by the control unit 230. For instance, if a certain medical milestone is achieved, a doctor, nurse, or other medical professional at the remote monitoring device may determine that a medicine administering schedule should be stopped. The medical milestone may be a positive milestone, e.g., a reduced or non-detectable viral load, or may be a negative milestone, e.g., determining that the patient is not responding to the medicine to achieve a desired result. Similarly, a notification that a tampering of the device 200 has been detected may cause a professional at the remote monitoring device to determine that the medicine should be neutralized. In either case, an instruction may be generated and sent for the device 200 to receive at the control unit 230 via the transceiver 239, directing the device 200 to neutralize the remaining medicine in the chamber 220. The interactions of a storage device, such as device 200 of FIG. 2 or device 100 of FIG. 1, with an example medicine dispensing machine or a remote monitoring device over one or more communication networks is described in greater detail below in connection with the example system 300 of FIG. 3. Additional variations and enhancements to the device 200 may be provided in various examples of the present disclosure. For example, medicine chamber 220 may store a variety of medicines which may be dispensed together, or in a staggered fashion.

Similarly, multiple neutralizing components may be included in a single storage device. For example, a powder neutralizing agent and a UV light source may both be included for neutralizing a medicine, or multiple medicines stored in the storage device. As just one example, hydrogen peroxide and titanium dioxide may be effective at promoting photo-degradation of oseltamivir (an antiviral/flu medication) in the presence of UV light. Thus, these and other modification are all contemplated within the scope of the present disclosure.

Figure 3:
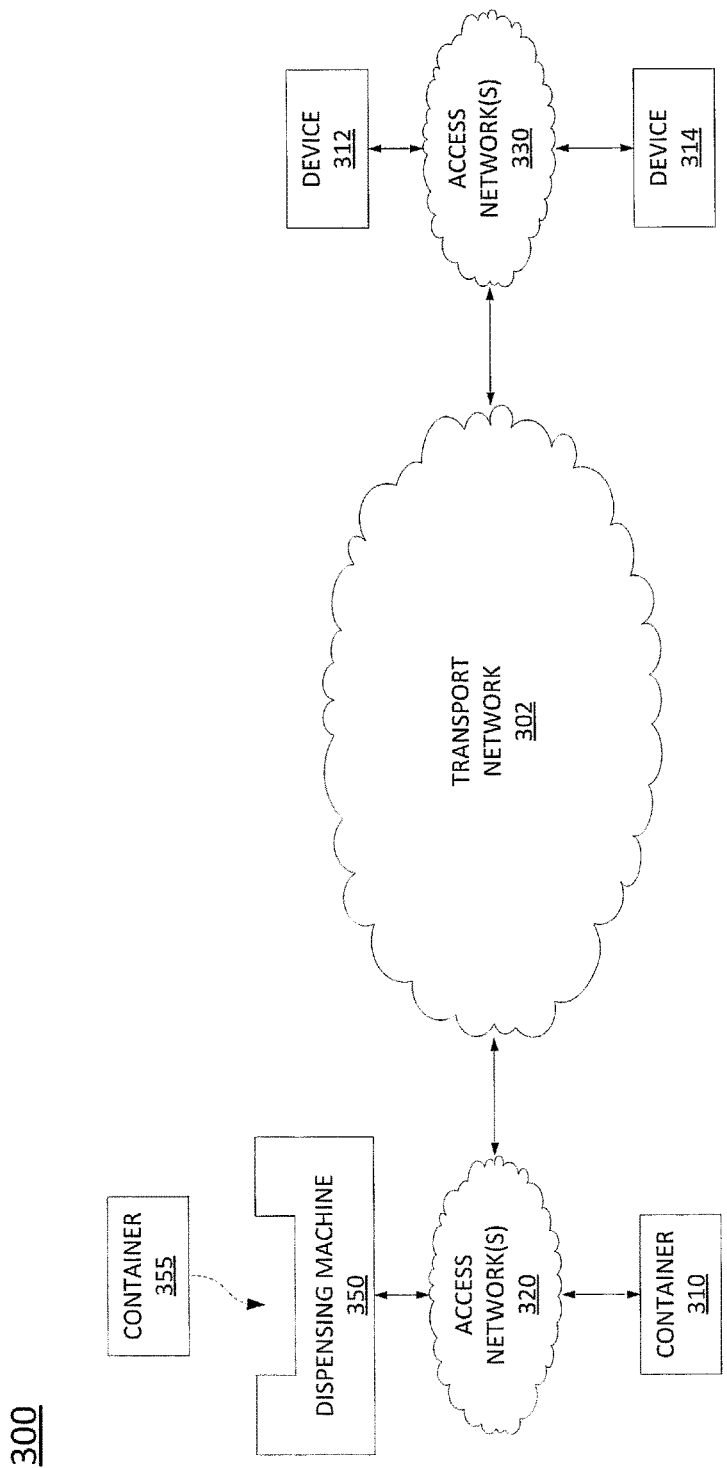
FIG. 3 illustrates an example system related to the present disclosure.

FIG. 3 is a block diagram depicting one example of a network or communications system 300 related to examples of the present disclosure. The overall communications system 300 may include any number of interconnected networks which may use the same or different communication technologies, such as a traditional circuit switched network (e.g., a public switched telephone network (PSTN)) or a packet network such as an Internet Protocol (IP) network (e.g., an IP Multimedia Subsystem (IMS) network), a multi-protocol label switching (MPLS network), a frame relay network, an asynchronous transfer mode (ATM) network, a wireless network, a cellular network (e.g., 2G, 3G, and the like), a long term evolution (LTE) network, and so forth. It should be noted that an IP network is broadly defined as a network that uses Internet Protocol to exchange data packets.

As illustrated in FIG. 3, system 300 may include a transport network 302. In one example, the transport network 302 may be operated by a telecommunications service provider. In one embodiment, the transport network 302, broadly a "communications network," may be in communication with one or more access networks 320 and 330. The access networks 320 and 330 may include a wireless access network (e.g., an IEEE 802.11/Wi-Fi network and the like), a cellular access network, a PSTN access network, a cable access network, a digital subscriber line (DSL) network, a metropolitan area network (MAN), other types of wired access networks, an Internet service provider (ISP) network, and the like. In one embodiment, the access networks 320 and 330 may all be different types of access networks, may all be the same type of access network, or some access networks may be the same type of access network and other may be different types of access networks. The transport network 302 and the access networks 320 and 330 may be operated by different service providers, the same service provider or a combination thereof. Alternatively, or in addition, access networks 320 and 330 may represent corporate, governmental or educational institution LANs, a home/residential LAN, and the like.

In the example of FIG. 3, either or both of the containers 310 and 355 may comprise a device for storing a medicine as illustrated in FIG. 1 or FIG. 2, and as described above, e.g., having at least a control unit and a transceiver for communicating with dispensing machine 350 and/or devices 312 and 314. In one example, containers 310 and 355 may each comprise a computing system, such as computing system 500 depicted in FIG. 5, and may be configured to provide one or more functions for neutralizing a medicine, as described in connection with the example method 400 of FIG. 4, and/or as described elsewhere herein. It should be noted that "configuring" an electrical device may comprise the loading of instructions or machine readable codes onto the electrical device. Said another way, one or more electrical signals can be applied to the electrical device to configure the device to perform one or more described functions. Furthermore, it should be noted that "configuring" an electrical-mechanical device may comprise the loading of instructions or machine readable codes onto the electrical-mechanical device and/or implementing structural features (e.g., of appropriate size, shape and material) to bring about one or more described electrical and/or mechanical functions.

As illustrated in FIG. 3, the container 355 may plug-in to dispensing machine 350 or may be cable-connected to the dispensing machine 350. Thus, container 355 may include a PCIe PHY, a SCSI transceiver, or the like, or a radio frequency (RF) wireless transceiver, e.g., for IEEE 802.11, Bluetooth, and/or BLE communications, and so forth. In this regard, dispensing machine 350 may include a complementary transceiver for using a same type of communication interface as the container 355. The dispensing machine may use the same transceiver or may include a different transceiver for communicating with devices 312 and 314 via access network 320. In one example, container 355 may store a medicine administering plan and transfer the medicine administering plan to the medicine dispensing device 350. For instance, the medicine administering plan may include details regarding medical milestones, such as a target concentration of the medicine in a patient's bloodstream, or the like. In addition, in one example, the dispensing device 350 may include testing tools to measure various patient biometrics. Accordingly, the medicine dispensing device 350 may vary the dosing, the scheduling of delivery of various doses, and so forth according to the medicine administering plan. For example, the dispensing device 350 may send instructions to container 355 to release a certain quantity of medicine at a certain time based upon patient biometrics and according to the medicine dispensing plan.

In one example, transport network 302 and access networks 320 and 330 may transmit and receive data communications between devices 312 and 314, dispensing machine 350, and containers 310 and 355 relating to the usage of medicines in containers 310 and 355. In one example, devices 312 and 314 may each comprise a mobile device, a cellular smart phone, a laptop computer, a tablet computer, a desktop computer, a smart television, a server, a cluster of such devices, and the like. For example, devices 312 and 314 may comprise remote monitoring devices that may be used by a doctor, a nurse, a clinician, and the like to monitor the use of dispensing machine 350 and/or containers 310 and 355. The monitoring may include receiving notifications from containers 310 and 355 and/or dispensing machine 350 regarding a dosage, a timing of a dose, a remaining quantity of medication in one of the containers, and so on. The monitoring may also include receiving notifications regard test results relating to one or more patient biometrics as described above, or receiving notifications regarding a tampering of one of the containers 310 or 355. In one example, communications with containers 310 and 355 may be via the dispensing machine 350 acting as an intermediary.

The monitoring may also include sending instructions to containers 310 and 355, and/or dispensing machine 350 regarding a modification to a medicine administering plan, such as a change in dosage, a timing of doses, and so on. In one example, devices 312 and 314 may also send instructions to container 310 or container 355 to neutralize a medicine contained therein, e.g., in response to receiving a notification of a tampering of the container, or in response to receiving a notification of information that indicates a treatment milestone in the administration of the medicine has been reached. In one example, devices 312 and 314 may each comprise a computing system or server, such as computing system 500 depicted in FIG. 5, and may be configured to provide one or more functions for remote monitoring and administration of a medicine dispensing machine or a networked medicine storage container, as described herein.

It should be noted that the system 300 has been simplified. In other words, the system 300 may be implemented in a different form than that which is illustrated in FIG. 3. For example, the system 300 may be expanded to include other network elements (not shown) such as border elements, routers, switches, policy servers, security devices, gateways, a content distribution network (CDN) and the like, without altering the scope of the present disclosure. Similarly, system 300 may omit various elements, substitute elements for devices that perform the same or similar functions and/or combine elements that are illustrated as separate devices. For example, device 312 or device 314 may comprise functions that are spread across several devices that operate collectively as a remote monitoring device. For instance, a remote monitoring device may comprise a virtual machine operating on one or more physical host devices in same location or distributed among several physical locations. In another example, device 312 or device 314 may alternatively be deployed in network 302. In addition, although two access networks 320 and 330, two devices 312 and 314, two containers 310 and 355, and one dispensing machine 350 are illustrated in FIG. 3, it should be understood that any number of access networks and devices may connect to the transport network 302.

In some examples, containers 310 and 355 may be designed to dispense medicine when connected to dispensing machine 350. However, in other examples, container 310 and/or container 355 may be equipped to dispense medicine according to a medicine dispensing plan without being required to couple to dispensing machine 350. For example, containers 310 and 355 may connect to a wireless access point, e.g., a wireless router for IEEE 802.11 communications, in access network 320 to communicate with devices 312 and 314 without connecting to dispensing machine 350 as an intermediary. Alternatively, or in addition, containers 310 and 355 may include cellular transceivers for communicating with devices 312 and 314. For instance, access network 320 may represent a cellular access network for connecting to transport network 302, access network 330, and other networks. The inclusion of a cellular communication component may help prevent a person from attempting to take one of containers 310 and 355 "off net."

For instance, in one example, a medical professional at device 312 may determine that the medicine in container 310 should be neutralized. However, if the patient is at home and turns off a wireless LAN connection, the container 310 may still likely be reachable via a cellular transceiver that cannot easily be turned off by the patient. In addition, containers 310 and 355 may also include testing modules for measuring various patient biometrics. In one example, if different medicines are to be administered to a same patient and call for the measurement of a same biomarker, the containers 310 and 355 may communicate directly with one another (peer-to-peer), via one or more networks, or via an intermediary device (such as dispensing machine 350), such that the same biomarker measurement is not duplicated. For instance, only a single blood draw may be used in connection with the administering of medicines from both of containers 310 and 355. Thus, these and other modifications of the system 100 are all contemplated within the scope of the present disclosure.

Figure 4:
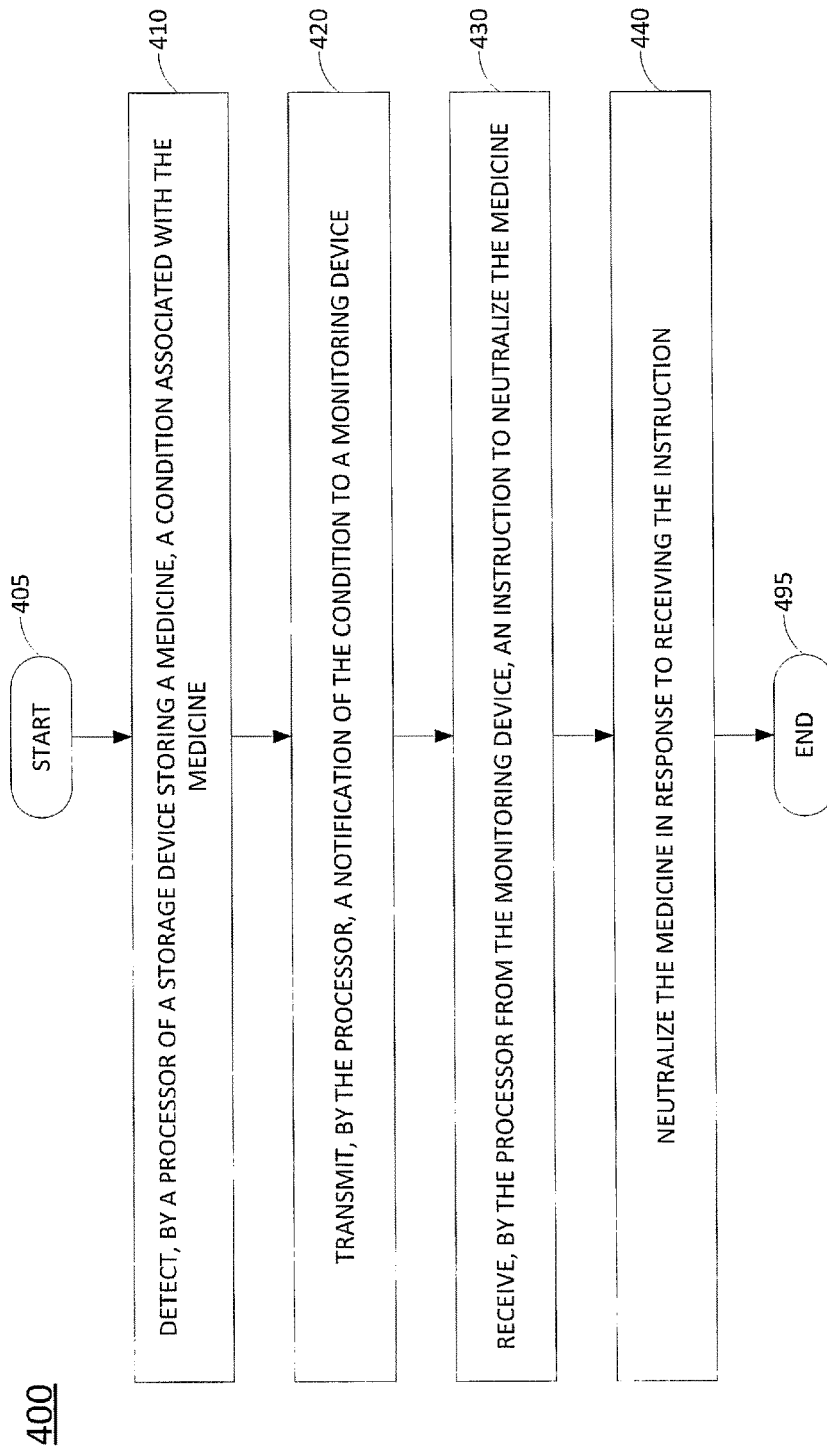
FIG. 4 illustrates a flowchart of an example method for neutralizing a medicine, in accordance with the present disclosure.

FIG. 4 illustrates a flowchart of an example method 400 for neutralizing a medicine, in accordance with the present disclosure. In one example, steps, functions and/or operations of the method 400 may be performed by a device storing a medicine, such a device 100 of FIG. 1, or device 200 of FIG. 2, and/or a control unit of such a device, a container, such as container 310 or container 355 in FIG. 3, and so forth. Alternatively, or in addition, the steps, functions, or operations of method 400 may be performed by a computing device or system 500, and/or processor 502 as described in connection with FIG. 5 below. For illustrative purposes, the method 400 is described in greater detail below in connection with an example performed by a processor, such as processor 502. For instance, processor 502 may represent a processor of a storage device storing a medicine.

The method begins in step 405 and proceeds to step 410. At step 410, the processor detects a condition associated with the medicine. For example, the condition may comprise a detection of a tampering of the storage device storing the medicine. The condition may also comprise a detection of a treatment milestone in an administration of the medicine to a patient associated with the storage device. However, the condition may simply comprise measurements or test results regarding various patient biometrics, without a conclusion that any particular milestone has been achieved. In still other examples, the condition may comprise a remaining quantity of medication, a percent of remaining charge of a battery of the storage device, and so forth.

At step 420, the processor transmits the notification of the condition to a monitoring device. In one example, the notification may be sent to a dispensing machine to which the storage device is connected. The dispensing machine may further communicate with another device, such as device of a physician, nurse, case worker, clinician, or other responsible medical professional, that may be deployed in another location. In another example, the processor may transmit the notification directly to a device of a medical professional via a wired or wireless connection (including a cellular connection) and/or via one or more intermediary networks.

At step 430, the processor receives an instruction to neutralize the medicine that is stored in the storage device. The instruction may be received via a same or a different communication pathway as the notification transmitted at step 420. For example, in response to receiving a notification of a tampering of the storage device, or in response to receiving a notification of information that indicates a treatment milestone in the administration of the medicine has been reached, a medical professional at a monitoring device, or the monitoring device executing a medicine administering plan in an automated manner, may determine that the medicine should be neutralized. Thus, an instruction may be generated at the monitoring device and sent to the processor of the storage device. In another example, a dispensing machine may be implementing a medicine administration plan associated with the medicine, storage device, and/or a patient associated with the storage device. Accordingly, in one example, a medicine administering plan may specify certain actions in response to certain conditions. For instance, the medicine administering plan may call for neutralizing the medicine if two instances of tampering with the storage device are detected. Alternatively, or in addition, the medicine administering plan may specify that the medicine should be neutralized after a certain period of time has expired, e.g., after two weeks, 30 days, etc., or after a certain treatment milestone is detected. Thus, the dispensing machine may automatically determine that the medicine should be neutralized and send an instruction back to the processor of the storage device. In other words, the determination to neutralize the medicine may be made automatically without further human input from a medical professional.

At step 440, the processor neutralizes the medicine in response to receiving the instruction. For instance, the processor may activate a neutralizing component, such as a heat, radiation or ozone source. Thus, step 440 may include applying a heat to the medicine, irradiating the medicine, or exposing the medicine to ozone. In another example, the processor may activate a neutralizing component in the form of a pellet, a powder, a liquid, or gel neutralizing agent that can chemically react with medicine and/or which can dissolve the medicine, rendering the medicine inert. For instance, the processor may dissolve or create an opening in a wall between chambers separating the medicine and the neutralizing agent. When the neutralizing agent and the medicine mix, the medicine may be rendered environmentally and/or biologically inert. Thus, the medicine may be safe to dispose in the environment or may be safe from potential use by a non-prescribed person or by a patient seeking to use the medicine in a non-prescribed way.

Following step 440, the method 400 proceeds to step 495. At step 495, the method 400 ends.

It should be noted that although not specifically specified, one or more steps, functions or operations of the method 400 may include a storing, displaying and/or outputting step as required for a particular application. In other words, any data, records, fields, and/or intermediate results discussed in the respective methods can be stored, displayed and/or outputted to another device as required for a particular application. Furthermore, steps or blocks in FIG. 4 that recite a determining operation or involve a decision do not necessarily require that both branches of the determining operation be practiced. In other words, one of the branches of the determining operation can be deemed as an optional step. In addition, one or more steps, blocks, functions, or operations of the above described method 400 may comprise optional steps, or can be combined, separated, and/or performed in a different order from that described above, without departing from the example embodiments of the present disclosure.

FIG. 5 depicts a high-level block diagram of a computing device suitable for use in performing the functions described herein. As depicted in FIG. 5, the system 500 comprises one or more hardware processor elements 502 (e.g., a central processing unit (CPU), a microprocessor, or a multi-core processor), a memory 504 (e.g., random access memory (RAM) and/or read only memory (ROM)), a module 505 for neutralizing a medicine, and various input/output devices 506 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 400 as discussed above is implemented in a distributed or parallel manner for a particular illustrative example, i.e., the steps of the above method 400, or the entire method 400 is implemented across multiple or parallel computing device, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method discussed above can be used to configure a hardware processor to perform the steps, functions and/or operations of the above disclosed method 400. In one embodiment, instructions and data for the present module or process 505 for neutralizing a medicine (e.g., a software program comprising computer-executable instructions) can be loaded into memory 504 and executed by hardware processor element 502 to implement the steps, functions or operations as discussed above in connection with the illustrative method 400. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 505 for neutralizing a medicine (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not a limitation. Thus, the breadth and scope of a preferred embodiment should not be limited by any of the above-described exemplary embodiments, but should be defined only in accordance with the following claims and their equivalents.

What is claimed is:

1. A storage device comprising:
    a chamber configured to store a medicine;
    a neutralizing component coupled to the chamber, wherein the neutralizing component comprises an ultraviolet light emitting diode;
    a transceiver configured to receive an instruction to neutralize the medicine; and
    a control unit comprising a processor, wherein the control unit is coupled to the transceiver, wherein the control unit is configured to neutralize the medicine by activating the neutralizing component when the instruction is received via the transceiver, and wherein the control unit is also configured to neutralize the medicine by activating the neutralizing component when a time has expired according to a medicine administering plan stored by the control unit.

2. The storage device of claim 1, wherein the control unit is further configured to transmit usage information associated with the medicine via the transceiver.

3. The storage device of claim 1, further comprising:
a tamper detection unit configured to detect a tampering of the storage device, wherein the control unit is for neutralizing the medicine when the tampering of the storage device is detected by the tamper detection unit.

4. The storage device of claim 3, wherein the tamper detection unit comprises an electronic mesh.

5. A device for storing a medicine, the device comprising:
a medicine chamber configured to store the medicine;
an intermediate chamber configured to store a neutralizing agent to neutralize the medicine, wherein a first wall between the medicine chamber and the intermediate chamber comprises a fluid-soluble material; and
an outer chamber configured to store a fluid, wherein the intermediate chamber and the outer chamber share a second wall.

6. The device of claim 5, wherein when the second wall is breached, the fluid is permitted to enter the intermediate chamber and dissolve the fluid-soluble material of the first wall.

7. The device of claim 5, wherein the neutralizing agent comprises a dry neutralizing agent.

8. The device of claim 5, further comprising:
a control unit, wherein the control unit comprises a processor.

9. The device of claim 8, wherein the control unit includes a dispensing channel coupled to the medicine chamber.

10. The device of claim 8, further comprising:
an opening unit controlled by the control unit, the opening unit for providing an opening in the second wall for the fluid to enter the intermediate chamber and to contact the first wall comprising the fluid-soluble material.

11. The device of claim 10, wherein the control unit is for opening the opening unit when a remote instruction is received.

12. The device of claim 10, wherein the control unit is for opening the opening unit when a time has expired according to a medicine administering plan stored by the control unit.

13. The device of claim 10, wherein the control unit is for opening the opening unit when a tampering of the device is detected via a tampering detection unit.

14. A method comprising:
detecting, by a processor of a storage device storing a medicine, a condition associated with the medicine;
transmitting, by the processor, a notification of the condition associated with the medicine to a monitoring device, wherein the monitoring device is external to the storage device;
receiving, by the processor, an instruction to neutralize the medicine from the monitoring device; and
neutralizing, by the processor, the medicine in response to receiving the instruction, wherein the processor is configured to neutralize the medicine when a time has expired according to a medicine administering plan stored by the control unit, wherein the neutralizing the medicine comprises irradiating the medicine via an ultraviolet light emitting diode.

15. The method of claim 14, wherein the condition comprises a detection of a tampering of the storage device storing the medicine.

16. The method of claim 14, wherein the condition comprises a detection of a treatment milestone in an administration of the medicine to a patient associated with the storage device.

* * * * *